United States Patent [19]

Philipson et al.

[11] 4,165,546

[45] Aug. 28, 1979

[54] PORTABLE CUSPIDOR

[76] Inventors: Alvin L. Philipson; Noel W. Abramson; Michael J. Woltcheck, all of 7321 Collins Ave., Miami Beach, Fla. 33141

[21] Appl. No.: 899,138

[22] Filed: Apr. 24, 1978

[51] Int. Cl.² .................. A61J 19/04; A61C 17/04
[52] U.S. Cl. .......................... 4/262; 4/263; 4/266
[58] Field of Search ............ 4/262, 263, 266, 264, 4/259, 265

[56] References Cited

U.S. PATENT DOCUMENTS

| 208,392 | 9/1878 | Holden | 4/259 |
| 1,103,832 | 7/1914 | Rackoff | 4/259 |
| 3,295,148 | 1/1967 | Deeley et al. | 4/263 |
| 3,400,412 | 9/1968 | Turner | 4/263 |
| 3,613,131 | 10/1971 | Stram et al. | 4/263 |

Primary Examiner—Lenard A. Footland
Attorney, Agent, or Firm—Ernest H. Schmidt

[57] ABSTRACT

A portable cuspidor supplied with rinse water and vacuum drainage through ganged flexible hoses has a hollow, enclosed cuspidor cup or bowl provided with a cushioned side wall opening against which facial areas surrounding the mouth of the patient or user are placed for expectorating. Interior rinse water jet streams are so directed and distributed against the interior of the cuspidor cup or bowl that substantially all of the rinse water, together with expectorant, will flow down for withdrawal at a drain orifice at the base of the bowl, no matter at what angle the device is being held for use.

6 Claims, 9 Drawing Figures

PORTABLE CUSPIDOR

This invention relates to portable self-rinsing cuspidors and is directed particularly to a novel and improved self-rinsing cuspidor.

Various portable cuspidors for use by dental patients and others in expectorating after rinsing the mouth, for example, are known. Such cuspidors differ principally from stationery cuspidors in that they are connected through flexible hoses to the sources of flush water and vacuum drain. Otherwise, the cuspidor bowl has been of conventional open-top configuration, requiring that the patient hold the device more or less at a level position while being used to prevent overflow of rinse water. At the same time it was necessary for the patient or other user to move his head and face over the open bowl properly to direct the expectorant in the bowl. This is all the more difficult when the user's mouth has been locally anesthetized, as in tooth filling for example. In such instances the patient often has a temporary loss of feeling in the areas of the mouth and lips, which makes it difficult to control spitting without such dribbling as might miss the expectorant bowl.

It is, accordingly, the principal object of this invention to provide a novel and improved portable cuspidor that obviates the deficiencies of such cuspidors heretofore devised.

A more particular object of the invention is to provide a novel and improved portable dental cuspidor wherein the cuspidor bowl or receptacle, instead of being open-topped, is in the form of a hollow enclosure with a cushioned side-wall opening against which facial areas surrounding the mouth of the patient can be placed, thereby insuring that all of the rinse expectorant or spittle will be discharged without loss into the interior of the cuspidor bowl for suction drain discharge.

Another object of the invention is to provide a portable dental cuspidor of the above nature wherein the opening in the hollow bowl enclosure is cushioned by use of a removeable ring gasket for sterilization and sanitation purposes.

Another object is to provide a portable dental cuspidor of the character described wherein the interior shape of the hollow cuspidor bowl is such, and the rinse water jet streams are of such force so directed and distributed, that substantially all of the rinse water will flow down into the vacuum drain orifice at the base of the bowl to minimize any possibility of drain water and expectorant spillage during use of the device. Such control, moreover, is effected no matter in what position the bowl might be placed for use by the patient, and even if used while the patient is reclining backwards in the dental chair.

And yet another object of the invention is to provide a portable dental cuspidor of the character described including a simplified and improved rinse water and drain vacuum operating valve in the handle of the device for ready use by the patient, and wherein drainage vacuum is supplied to the cuspidor bowl before turning on of the rinse jet stream, and the rinse jet stream is turned off before discontinuance of drainage vacuum, thereby minimizing the possibility of fluid remaining in the bowl after release or closure of the operating valve.

Yet another object of the invention is to provide a portable dental cuspidor of the character described which will be simple in construction, economical to manufacture, quiet in operation, attractive in appearance, and long wearing in use.

Other objects, features and advantages of the invention will be apparent from the following description when read with reference to the accompanying drawings. In the drawings.

Figure 1:
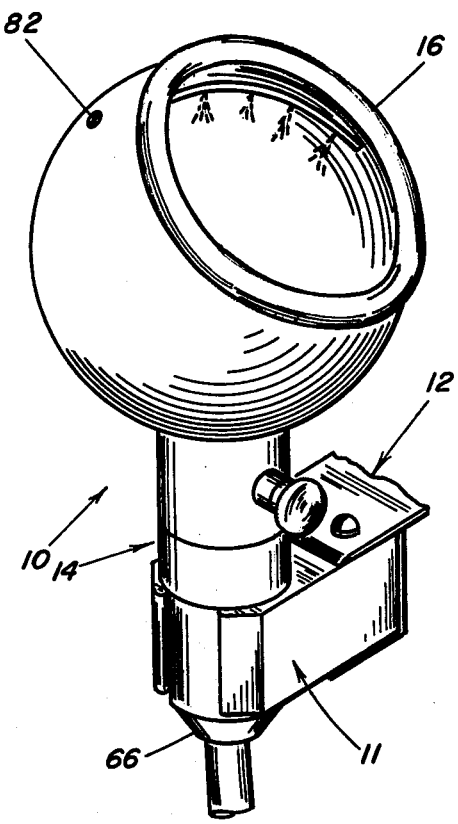
FIG. 1 is a perspective view of one form of portable dental cuspidor embodying the invention, shown at rest in its holder.

Referring now in detail to the drawings, reference numeral 10 in FIG. 1 designates, generally, a preferred form of portable dental cuspidor embodying the invention, the same being illustrated as supported in its holder 11. The holder 11 may be fixed with respect to the usual dental chair or associated apparatus (not illustrated), such as by a bracket 12, (see also FIG. 2), the location being convenient for ready use, either by the patient alone or with the help of a dental assistant, for example.

Figure 2:
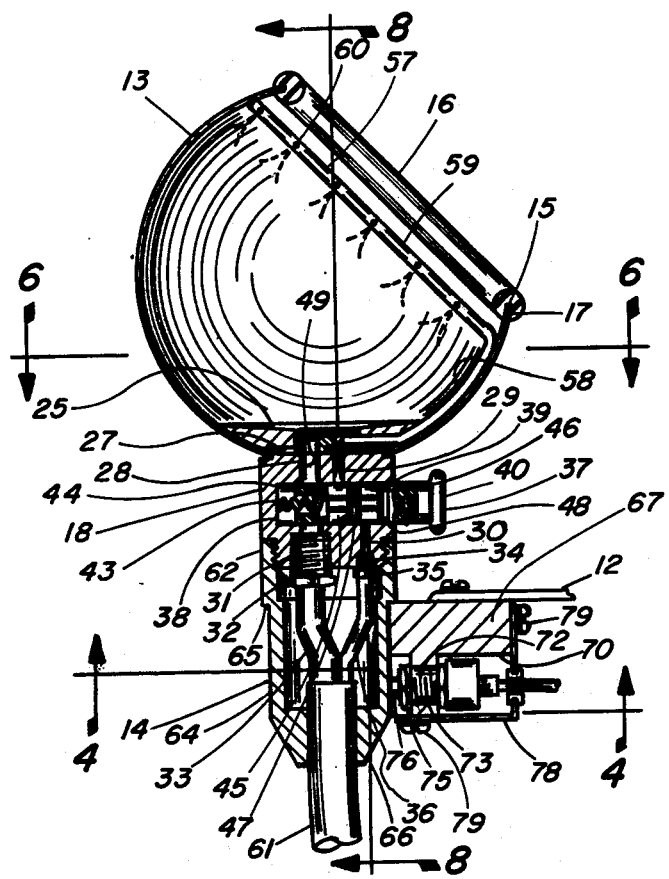
FIG. 2 is a vertical cross-sectional view of the dental cuspidor illustrated in FIG. 1, with the rinsing valve mechanism in normal or "off" position.
Figure 7:
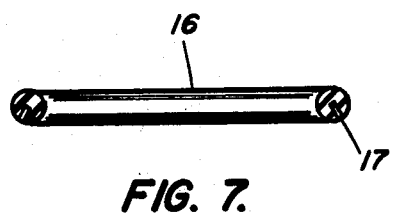
FIG. 7 is a transverse cross-sectional view of the cup member ring gasket, shown separately.
Figure 9:
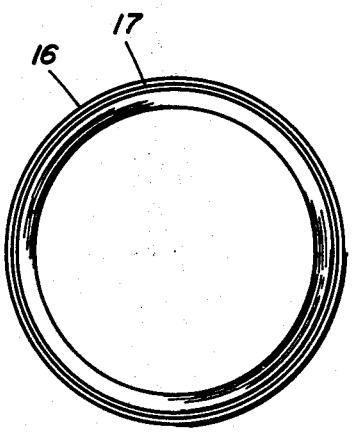
FIG. 9 is a bottom view of the ring gasket illustrated in FIG. 7, shown separately.

The portable dental cuspidor 10 comprises a cup member 13, which may be spherical in shape, for example, and which is attached to the upper end of a generally cylindrical handle structure 14, as is hereinafter more particularly described. The cup member 13 has an opening 15 which will preferably lie in a common plane and which, if said cup member is of spherical configuration, will be circular. As is best illustrated in FIG. 2, the cup member opening 15 lies in a plane defining an angle of approximately 45 circular degrees with the longitudinal axis of the handle structure 14, so as to be in convenient position for placement to the mouth when expectorating. The edge of the cup member opening 15 may be covered by removeable ring gasket 16, said ring gasket preferably being circular in cross-section and having a co-extensive radial slot 17 by means of which said gasket can be removeably attached to said cup member, (see also FIGS. 7 and 9). It will be understood that the ring gasket 16, which will preferably be fabricated of soft silicone rubber, or other high temperature resistant, hypoallergenic, resilient material serves as a cushion when applying the mouth and face to the cup member for expectorating. In this connection, it is to be noted that the ring-gasket 16 is readily removable for autoclaving or replacement, for which purpose the annular slot 17 is molded at an angle of approximately 45 degrees with respect to the axis of generation thereof for easy and secure attachment to the cup member opening 15.

The handle structure 14 comprises a cylindrical valve body member 18 which may be fabricated of lightweight metal or a tough synthetic plastic material, for example, the upper end of which is formed with a narrow, marginal, peripheral step or recess 19, and the lower end of which is provided with a reduced-diameter externally-threaded portion 20. Valve body member 18 has a diametrically-opposed pair of top to bottom through openings 21, 22 for the reception of machine screws 23, 24 (see FIG. 8) to be received in threaded openings in top cup clamp and drain member 25 fitted within the bottom of cup member 13, said cup member having a circular bottom opening 26 of such size as to fit snugly within the peripheral recess 19 of valve body member 18. A flat, circular rubber gasket 27 with appropriate openings therein for passage of machine screws 23 and 24, and conduits for vacuum and flush water delivery to the cup member as is hereinafter more particularly described, is fitted between top cap clamp and drain member 25 and valve body member 18. The member 25 is appropriately rounded about its peripheral edge to conform with the internal shape of the cup member 13 surrounding circular bottom opening 26 so as to effect tight interclamping connection of the parts by means of the assembly machine screws 23 and 24.

Manually controlled means is provided for supplying rinse water and vacuum suction to the interior of the cup member 13. To this end, a through vacuum opening 28 and laterally offset flush water openings 29, 30 are provided in the cylindrical valve body member 18. The lower end of through vacuum opening 28 communicates with an increased-diameter, internal pipe thread opening 31 screw-threaded within which is a nipple fitting 32 having attached thereto a flexible vacuum supply hose 33. The lower water opening 30 is similarly formed at its lower end with an increased-diameter, internally-threaded portion 34 screw-threaded within which is a comparatively small nipple fitting 35 having attached thereto a flexible water supply hose 36.

As means for controlling flow through the vacuum opening 28 and laterally offset water openings 29, 30, a cylindrical push member 37 is slidably disposed within a deep, diametrically-extending cylindrical opening 38 formed in cylindrical valve body member 18. The cylindrical push member 37 comprises a body portion 39 and a head portion 40 screw-threaded therein. The push member body portion 37 is removably contained within the cylindrical opening 38 by means of a locating screw 41 threaded through a counterbored bottom opening 42 in valve body member 18, (see FIG. 8) and extending vertically into annular recess 46 in push member body portion 39 as is hereinafter described. The inner end of the recess 46 is so located as to limit the outer position of the cylindrical push member 37 to the "off" position as illustrated in FIG. 2, under the influence of helical compression spring 43 constrained between the bottom wall of cylindrical opening 38 and the bottom wall of a co-axial cylindrical recess 44 formed in the inner end of cylindrical push member body portion 39. In such position, as illustrated in FIG. 2, peripheral wall portions thereof block communication between flexible vacuum supply hose 33 and the through vacuum opening 28 leading to cup member 13. At the same time, spaced annular recesses 45 and 46 formed along cylindrical push member body portion 39 and in communication with respective laterally-offset water openings 29 and 30 are not in communication with one another to permit through flow of water because of o-ring 47 seated within a recess formed about the periphery of the full diameter portion of said body portion between said annular recesses. The push member 37 therefore serves to shut off both vacuum and water supply to the cup member 13 when in its normal or rest position as illustrated in FIG. 2. In this connection, it is further to be noted that a second o-ring 48 seated within a recess formed about the periphery of the fulldiameter portion of cylinder push member body portion 39 adjacent outer annular recess 46 seals off said annular to prevent water under pressure leaking through to the outside of cylindrical valve opening 38.

Figure 3:
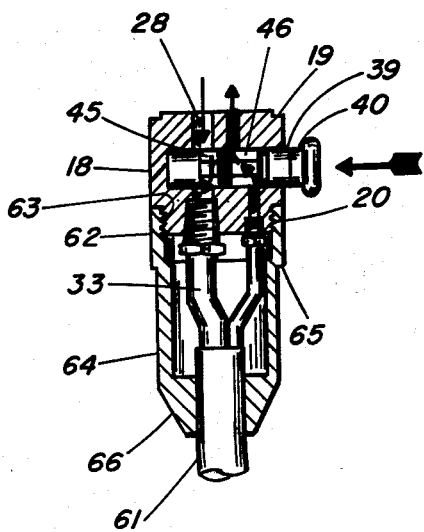
FIG. 3 is a vertical cross-sectional view of the handle and control valve mechanism, as in FIG. 2, but shown separately and with the control valve mechanism in "on" or actuated condition for flush rinsing and evacuation of the cuspidor.

In operation of the control valve, finger pressure will be applied to the push member head portion 40, pushing it into fully seated position within its cylindrical opening 38 against the yieldingly reactive force of compression spring 43. In such depressed position, illustrated in FIG. 3, the annular recess 45 will have been brought into substantial alignment with vacuum through opening 28, and recess 46 will have been brought in such position between laterally offset water openings 29 and 30 as to provide for intercommunication therebetween. Thus vacuum and water under pressure supplied through hoses 33 and 36, respectively, will be brought into communication with the interior of the cup member 13 through the upper end of the valve body member 18 whereas said cup member is attached as is herein above described. In this connection it is to be noted that the o-ring 47 serves to separate the vacuum and water pathways, thereby preventing aspiration into opening 28 of supply water being fed through water inlet openings 29 and 30.

Figure 5:
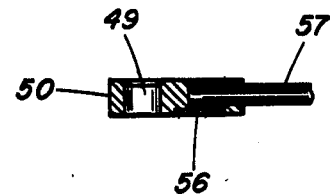
FIG. 5 is an enlarged, vertical cross-sectional view, shown separately and on an enlarged scale, of the insert disc comprising the top cap clamp and drain member illustrated in FIG. 2.
Figure 8:
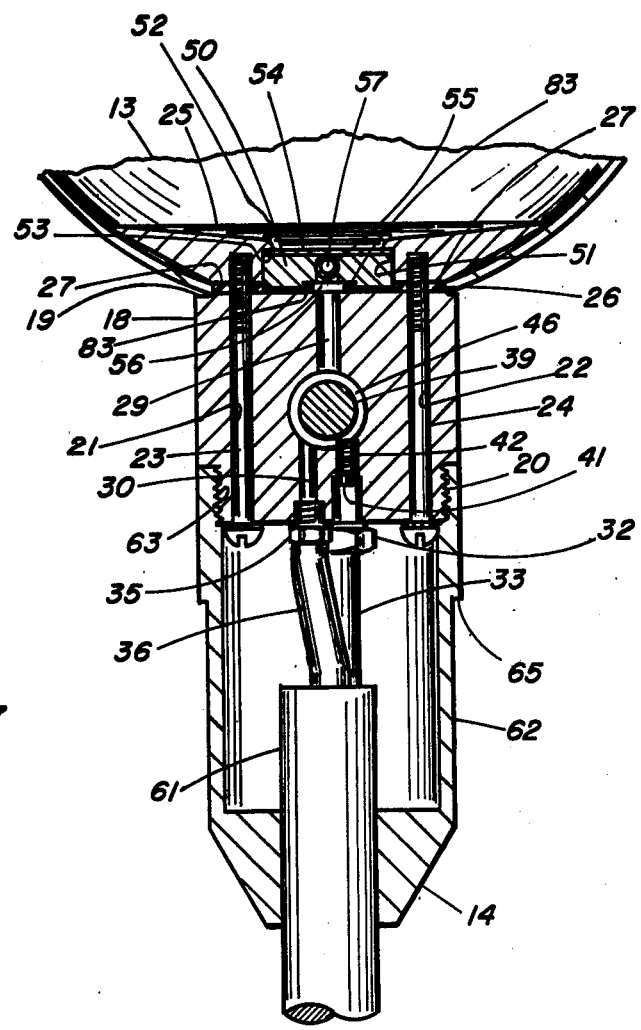
FIG. 8 is a partial vertical cross-sectional view of the dental cuspidor, taken along the line 8—8 of FIG. 2 in the direction of the arrows on an enlarged scale, and further illustrating constructional details.

Referring to FIGS. 2, 5, and 8, it will be seen that the circular top cap clamp and drain member 25 is provided with a through opening 49 which is aligned with vacuum opening 28 in the valve body member 18, thereby defining a suction drain opening in the upper surface of said clamp and drain member. The through vacuum opening 49 is formed in an insert disc 50 comprising top cap clamp and drain member 25, which is brazed or otherwise secured within a conforming cylindrical recess 51 in the bottom of said clamp and drain member (see FIG. 8). Cylincrical recess 51, opens into a reduced-diameter, central opening 52 in the clamp and drain member 25 to provide an internal shoulder 53 against which a perforated disc strainer 54 is seated and retained in place by insert disc 50. The perforated disc or screen 54 prevents aspiration of expectorated dental debris through the vacuum system.

A radially-extending recess 55 communicating with a vertically-extending opening 56 within the underside of insert disc 50 has brazed or otherwise secured therein a substantially rigid water rinse tube 57. As illustrated in FIG. 2 the vertically-extending opening 56 is located to be in communicating alignment with the water opening 29 in cylindrical valve body member 18, so that rinse water will be fed through the water rinse tube 57 whenever the cylindrical push rod member 37 is manually depressed for operation of the device. A small o-ring 83 fitted in a counterbored opening at the underside of insert disc 50 and concentric with water opening 29 serves to seal the water passageway. As illustrated in FIGS. 1 and 2, the water rinse tube 57 is of such configuration along its length as to extend upwardly along an inside bottom portion of the cup member 13, as indicated at 58, and thereafter partially encircle an inside marginal portion of said cup member near the mouth opening thereof as indicated at 59. The water rinse tube is provided with a plurality of spaced openings 60 along its length directing spray water along substantially all inside surface portions of the cup member 13 to continually wash the interior thereof whenever the device is being used.

The flexible vacuum and water supply hoses 33 and 36 are enclosed in a common protective sleeve 61 through which they pass for interconnection with the water and vacuum supply systems normally provided with associated dental chair stations and apparatus. The handle structure 14 also comprises a cylindrical cover sleeve 62 through which the protective sleeve 61 for the hose assembly passes, said cover sleeve having an internally-threaded upper end portion 63 threadingly engageable with the reduced-diameter, externally-threaded portion 20 of the valve body member 18 for removable interconnection thereto. The outer periphery of the internally-threaded end portion 63 of the sleeve 59 merges with a reduced-diameter lower end portion 64 to define thereat an annular shoulder 65. The lower end of the reduced-diameter portion 64 terminates in a frusto-conical portion 66.

Figure 4:
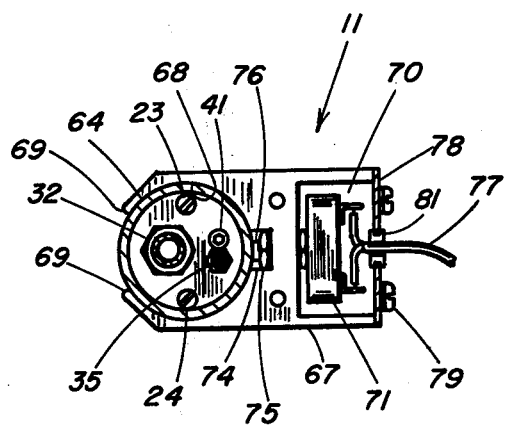
FIG. 4 is a horizontal cross-sectional view taken along the broken line 4—4 of FIG. 2 in the direction of the arrows and illustrating constructional details of the dental cuspidor holder and its mechanism for automatically switching off the vacuum supply when the device is not being used.
Figure 6:
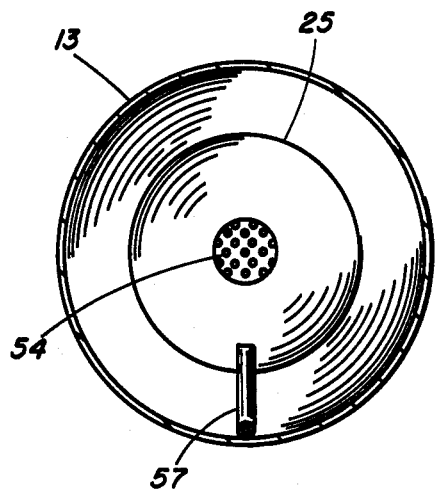
FIG. 6 is a horizontal cross-sectional view taken along the line 6—6 of FIG. 2.

With reference to FIGS. 1, 2, and 4, the holder 11 for the portable cuspidor 10 when not being used, comprises a support block member 67 of generally rectangular shape and having a cylindrical through opening 68 of such diameter as to receive, slide fitted therein, the reduced-diameter lower end portion 64 of handle structure cover sleeve 62. Thus, as illustrated in FIG. 2, when the dental cuspidor 10 is placed in rest position in the holder 11, the annular shoulder 65 will seat upon the upper surface of the holder support block member 67. As illustrated in FIGS. 1 and 4, support block member 67 of the holder 11 is formed with a front opening 69 to allow for passage of the supply cable sleeve 61 through handle opening 68. It will be understood that the frusto-conical shape at the lower end of the handle structure 14 facilitates the guidance of the dental cuspidor assembly into the cylindrical locating opening 68 in the holder 11.

As illustrated in FIGS. 2 and 4, the underside of the support block member 67 is provided with a rectangular recess 70, open at the back, within which is located a normally closed electrical push-button switch 71, the actuating button shank 72 of which extends through a forwardly-extending bore 73 openinto a recess 74 merging with cylindrical through opening 68 near the lower end thereof. The push button switch 71 is retained in place by nut 75, and said switch is so located that its actuating push-button 76 extends into the cylindrical through opening 68. Thus, whenever the portable dental cuspidor 10 is placed at rest position in the holder 11, the electrical switch push-button 76 will be depressed for open-circuiting the electrical switch 71. An electrical cable 77 connected to an energizing circuit (not illustrated) for the vacuum supply system serving the various vacuum controlled facilities of the associated dental station, serves to automatically discontinue vacuum production whenever none of the associated vacuum actuated devices or apparatus (not illustrated) is being used. An angular cover plate 78 removably secured to the support block member 67 as by machine screws 79 serves to enclose rectangular block recesses 70 and 74. The switch cable 77 extends through a grommet 81 in the cover plate 78.

As illustrated in FIG. 1, a small through opening 82 is provided in the cup member 13 to eliminate the possibility of any objectionable suction forces being applied to the face of a patient, who upon use of the cuspidor, places facial portions in more or less sealing contact against the ring gasket 16.

An important advantage of the invention resides in the fact that the interior rinse water jet streams are so directed and distributed against the interior of the cuspidor bowl, that substantially all the rinse water, together with the expectorant, will flow down for suction withdrawal at the drain opening at the base of the bowl, regardless of the angle at which it is being held in use by the patient. Thus, the patient can easily make use of the cuspidor, whenever needed and no matter what his position in the dental chair, and without the necessity of bending over the top of the cuspidor, as required with prior portable cuspidor devices.

While we have illustrated and described only one form in which our invention can conveniently be embodied in practice, it is to understood that this form is presented by way of example only and not in a limiting sense herein. For example, although the portable cuspidor is described herein as a dental cuspidor, it is not limited to such use, and can be used as well in other situations where there is a need to expectorate into an automatic sanitary discharge system. Also, instead of using water as a rinsing agent, antiseptic solutions could alternatively be used, to be discharged as waste or to be filtered and recirculated in a closed system. Our invention, in brief, comprises all the embodiments and modifications coming within the scope and spirit of the following claims.

What we claim as new and desire to secure by Letters Patent is:

1. A portable cuspidor comprising, in combination, a cup member, a handle for said cup member, drain opening means in said cup member, a first flexible hose means communicating with said drain opening means for the drainage of fluid from said cup member, a second flexible hose means for supplying rinse fluid under pressure to said cup member, said cup member defining a substantially closed chamber except for an access opening large enough for the placement of facial portions surrounding the mouth thereagainst for expectorating into said cup member, and multiple jet conduit means communicating with said rinse fluid supply means for discharging rinse fluid against interior surface portions of said cup member for drainage through said drain opening means and said fluid drainage means, said first flexible hose means comprising a vacuum hose for aspirating discharge fluid from said cup member, said second flexible hose means comprising a fluid hose, said cup member being substantially in the form of a spherical section defining an access opening having a curved edge, and a removable ring gasket secured to the peripheral edge of said access opening in said cup member.

2. A portable cuspidor as defined in claim 1 wherein said handle is of elongated configuration extending radially outwardly of said cup member and defining an angle of approximately 45 degrees with respect to the plane of said access opening.

3. A portable cuspidor as defined in claim 2 wherein said ring gasket is circular in cross-section and formed with a peripheral, radially-extending slot defining an angle of approximately 45 degrees with respect to the axis of generation of said ring gasket.

4. A portable cuspidor as defined in claim 1 wherein said handle is substantially cylindrical in shape and wherein said vacuum and fluid hoses extend longitudinally into the interior of said handle.

5. A portable cuspidor as defined in claim 4 including valve means in said handle for substantially simultaneously controlling the communication of said vacuum hose and said fluid hose with said cup member.

6. A portable cuspidor as defined in claim 5 wherein said valve means comprises a diametrically-extending cylindrical opening formed in said handle, a cylindrical valve push member slidably received within said cylindrical opening and movable between inner and outer limit positions, resilient means normally constraining said push member in its outer limit position, and means controlled by manually depressing said push member to said second limit position for actuating said communication controlling means.

* * * * *